United States Patent [19]

Potts

[11] Patent Number: 5,280,789

[45] Date of Patent: Jan. 25, 1994

[54] APPARATUS AND METHOD FOR MEASURING FLUID PRESSURE IN A MEDICAL PATIENT

[76] Inventor: Richard A. Potts, 4760 Pacific Hwy., Bellingham, Wash. 98226

[21] Appl. No.: 828,405

[22] Filed: Jan. 31, 1992

[51] Int. Cl.$^5$ .............................................. A61B 5/02
[52] U.S. Cl. ..................................... 128/673; 128/672; 33/379
[58] Field of Search ................. 33/369, 379, 384, 385; 312/245, 246, 249.1, 349; 24/3 F; 128/672–675

[56] References Cited

U.S. PATENT DOCUMENTS

| | | | |
|---|---|---|---|
| 3,495,585 | 2/1970 | Halligan et al. | 128/674 |
| 3,693,612 | 9/1972 | Donahoe et al. | 128/674 |
| 3,996,927 | 12/1976 | Frank | 128/673 |
| 4,546,774 | 10/1985 | Haught | 128/673 |
| 4,669,484 | 6/1987 | Masters | 128/674 |
| 4,691,710 | 9/1987 | Dickens et al. | 128/673 |
| 5,054,170 | 10/1991 | Otrusina | 24/3 F |
| 5,168,235 | 12/1992 | Bonner | 33/379 |

OTHER PUBLICATIONS

Production specification sheet from Applied Laser Systems, 2160 NW Vine St., Grants Pass, OR 97526.
Description of Pressure Monitor SP1405, date, author and publication unknown. (5 pages including drawings).
Hudak et al, Critical Care Nursing, 1977, pp. 185–193.

*Primary Examiner*—Kyle L. Howell
*Assistant Examiner*—Robert L. Nasser, Jr.
*Attorney, Agent, or Firm*—Hughes & Multer

[57] ABSTRACT

An apparatus for vertically aligning a given point on a pressure transducer unit with a desired point an a patient, the apparatus comprising: (a) a light source; (b) a housing adapted to contain the light source; (c) at least one leveling tube having a leveling axis that is substantially parallel to the light beam, the leveling tube comprising (i) a closed transparent envelope containing a liquid and a bubble of gas, and (ii) lines formed on the envelope, where the leveling axis is substantially horizontally aligned when the bubble of gas is located between the two lines; (d) an indicating mark formed on the housing means, where the beam of light is vertically aligned with the given point on the transducer unit when the indicating means is vertically aligned with the given point on the transducer unit; and (e) a locking system for selectively locking the housing means to prevent movement thereof relative to the transducer unit when the beam of light is both horizontally aligned and vertically aligned with the given point on the transducer unit. To vertically align the given point with the desired point, one of the transducer unit and the patient are vertically displaced relative to the other until the light source causes light to reflect off of the patient at the desired point.

20 Claims, 4 Drawing Sheets

APPARATUS AND METHOD FOR MEASURING FLUID PRESSURE IN A MEDICAL PATIENT

TECHNICAL FIELD

The present invention relates to fluid measuring apparatus and methods and, more particularly, to such apparatus and methods used to measure blood pressure in the right atrium of a patient's heart.

BACKGROUND OF THE INVENTION

The present invention is particularly useful for monitoring a patient's central venous pressure. Accordingly, that application will be discussed in the following detailed description. However, the present invention may have application in situations where other bodily fluid pressures are to be measured. The scope of the present invention should therefore be determined by the attached claims and not the following detailed description.

Central venous pressure (CVP) is the pressure of blood in the right atrium or vena cava of a human heart. A patient's CVP provides important information about the patient such as: (a) the patient's blood volume; (b) the effectiveness of the patient's heart as a pump; and (c) the patient's vascular tone. Therefore, in combination with a clinical assessment of the patient, a health care worker will often monitor the patient's CVP, and particularly any upward or downward trends in CVP, to determine whether and what type of intervention is appropriate for the patient.

CVP is normally measured in terms of centimeters or millimeters of water pressure. A typical pressure in the right atrium is 0 to 4 cm $H_2O$, while pressure in the vena cava is approximately 6 to 12 cm $H_2O$.

Figure 3:
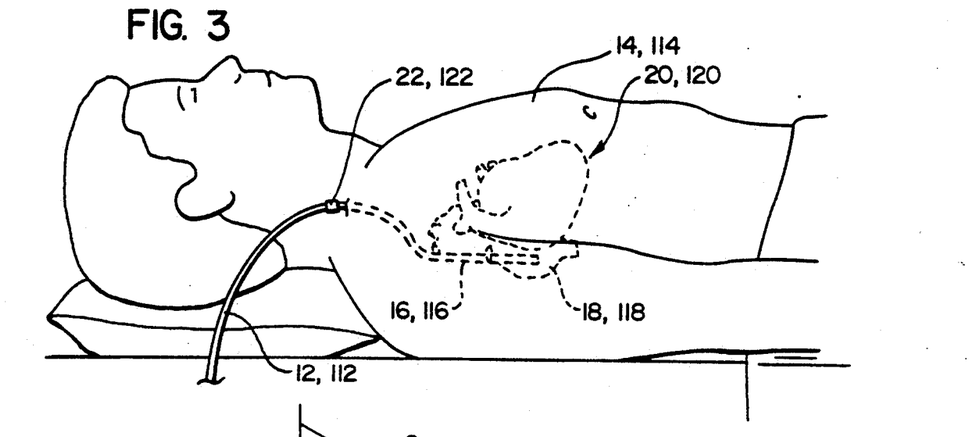
FIG. 3 is a side, schematic view depicting the placement of a catheter used to determine central venous pressure of a patient.

One method of measuring CVP is to insert a catheter into an arm or leg vein or the subclavian vein and thread the catheter through the vein into the vena cava close to the right atrium. FIG. 3 depicts a catheter inserted through the subclavian vein into the vena cava. A manometer or other pressure measuring device is then attached to second end of the catheter through intravenous (IV) connecting tubing. If a manometer is used, pressure in the vena cava displaces or equilibrates with the pressure exerted by the column of fluid in the manometer and the point at which the fluid in the manometer settles is the recorded as the CVP.

In a modern hospital setting, the pressure measuring device is typically a pressure transducer which generates an electrical signal corresponding to the pressure at the end of the IV connecting tubing. Such pressure transducers generally comprise a diaphragm so arranged that the diaphragm is measurably displaced by the pressure in the IV connecting tubing. The electrical signal generated by the transducer is proportional to the displacement of the diaphragm. Because displacement of the diaphragm is proportional to CVP, the magnitude of the electrical signal can thus be empirically related to CVP. Properly calibrated with equipment for analyzing these electrical signals, a pressure transducer allows the health care worker to accurately measure and monitor trends in CVP.

In order to obtain an accurate measurement of CVP, the zero point of the manometer or a given measuring point on the pressure transducer must be closely vertically aligned with a desired point on the patient such as a mark corresponding to the patient's right atrium and/or vena cava. If the vertical level of the point at which pressure is measured is below the right atrium, the CVP reading will be too high. On the other hand, if the vertical level of this measuring point is higher than the right atrium, the CVP reading will be too low.

Perhaps even more importantly, if the vertical level of one of the right atrium and the measuring point changes over time while the other of these vertical levels remains the same, CVP may appear to trend upwardly or downwardly when actual CVP has remained constant or, alternatively, an actual upward or downward trend in CVP may be masked by the change in measured CVP. This may result in the health care worker providing inappropriate intervention. Accordingly, consistency in aligning the pressure monitoring device in relation to the right atrium over time is perhaps more important than accurately aligning the pressure monitoring device with the right atrium.

The consequences of not consistently aligning the pressure monitoring device with the right atrium of the heart can be quite serious. For example, if: (a) a first CVP measurement is taken at time $t_1$; (b) the patient subsequently moves or is moved so that the patient's right atrium is lower than at time $t_1$; (c) by time $t_2$ the patient's actual CVP raises, indicating higher blood pressure; and (d) a second CVP measurement is taken at time $t_3$, the second CVP measurement may not reflect the rise in CVP that occurred between time $t_1$ and time $t_2$. The health care worker may mistakenly assume that CVP is constant and no intervention is necessary, while in fact the higher actual CVP may indicate third spacing of bodily fluids caused by increased blood volume and pressure. In this case, the appropriate intervention, i.e., halting the flow of intravenous fluids into the blood stream, may not be taken. Serious problems may thus be hidden by a pressure transducer that is improperly vertically aligned with the right atrium of the heart.

It is therefore essential that the pressure measuring device be consistently and accurately aligned with the right atrium of the heart so that actual CVP and upward and downward trends in CVP are accurately monitored.

PRIOR ART

Figure 1:
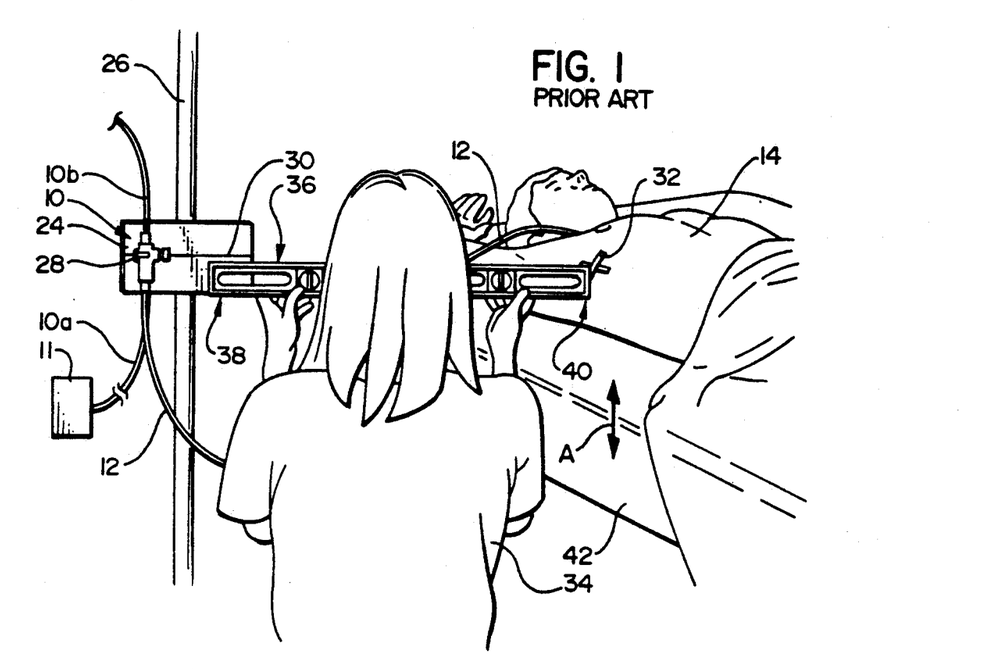
FIG. 1 is a perspective, environmental view depicting a prior art method of measuring a patient's central venous pressure.

Depicted in FIG. 1 is the industry standard prior art method of measuring blood pressure in the right atrium of the heart. In FIG. 1, the pressure monitoring device is a transducer unit indicated at reference character 10. The transducer 10 may be, for example, a transducer model number TXX-R Pressure Transducer 3CC manufactured by Viggo Spectromed. This transducer may be purchased in the 60 inch transducer kit for pole mount applications, model number T4812AD-4 also manufactured by Viggo Spectromed.

A length of IV connecting tubing 12 extends from a patient 14 to the transducer unit 10. As depicted in FIG. 3, a catheter 16 has been inserted into the patient's subclavian vein and threaded through this vein into the right atrium 18 of the patient's heart 20. The catheter 16 is connected at 22 to the IV connecting tubing 12. The catheter 16 and IV tubing 12 are filled with fluid; thus, the pressure of blood in the right atrium 18 is transmitted to the fluid within the catheter 16 and tubing 12 where this pressure can be measured by the transducer 10.

Referring back to FIG. 1, the transducer unit 10 is attached to a mounting bracket 24 which is slideably and rotatably mounted on a vertically extending pole 26. The vertical level of a given measuring point 28 of the transducer unit 10 is indicated by a line 30 formed on the bracket 24. In the preferred embodiment, the measuring point 28 is at the balancing port of the transducer unit 10.

The transducer unit 10 further comprises a cable 10a through which electrical signals related to sensed pressure are transmitted to an analyzing device 11 that calculates and records CVP based on these electrical signals. The analyzing device 11 may be, for example, a CVP module model number M1006A manufactured by Hewlett Packard and designed to be plugged into Hewlett Packard's Component Monitoring System model number 56-M117A.

A second length of IV connecting tubing 10b extends from the top of the transducer unit 10 to container (not shown) containing an IV solution to be introduced into the patient 14. This allows fluid within the tubing 12 to be flushed and to allow introduction of intravenous fluids and medications into the patient's bloodstream as necessary.

The vertical level of the right atrium 18 of the patient's heart 20 generally corresponds to the midaxillary line of the patient 14 and is marked by an X-mark 32 formed on the patient 14 approximately 5 cm below the patient's sternum. While this X-mark may not be precisely aligned with the patient's right atrium in all cases, the X-mark is actually formed on the patient with indelible ink so that measurements may at least be consistent over time.

To align the measuring point 28 of the transducer unit 10 with the end of the catheter 16 located within the right atrium 18, a health care worker 34 uses a leveling device such as a conventional three-foot carpenter's level 36. Alternatively, the leveling device may be a length of rigid material such as a wooden yardstick having a known bubble indicator attached to the center portion thereof to indicate when the yardstick is horizontal.

A first end 38 of the carpenter's level 36 is initially placed along the line 30 formed on bracket 24. The health care worker 34 then raises and lowers the second end 40 of the level 36 until the horizontal bubble indicator (not shown) on the level 36 indicates that the level 36 is horizontally aligned. When the level 36 is horizontally aligned, the worker 34 determines whether the second end 40 of the level 36 is aligned with the X-mark 32.

If the end 40 is not aligned with the X-mark 32, the worker 34 must raise or lower as appropriate, in the direction indicated by the arrow A, either the patient 14 by raising and lowering the patient's bed 42 or the transducer unit 10 by raising and lowering the bracket 24 on which the transducer unit 10 is mounted. In either case, the worker 34 cannot continue to hold the level 36 such that it is vertically aligned because to do so requires two hands and at least one hand, and preferably two hands, must be free to adjust the bed 42 or bracket 24. The worker 34 must therefore set the level 36 down, adjust the bed 42 or bracket 24, and then raise and horizontally align the level 36 to check whether the X-mark 32 is properly aligned with the level end 40. This process is repeated until the end 40 of the horizontally-aligned level 36 is vertically aligned with the X-mark 32.

It should be clear that a major problem with the prior art method depicted in FIG. 1 is that, for one person, the task of aligning the transducer unit 10 with the X-mark is time consuming and onerous. While two workers may more easily perform this just-described alignment method, for cost and scheduling reasons, it is usually preferable that this task be performed by only one worker.

Another major problem with the prior art method shown in FIG. 1 is that it may be inaccurately performed, especially when performed by one person. This is because it is quite difficult to hold the level 36 in its horizontally aligned position while determining whether the end 40 thereof is aligned with the X-mark 32. When the worker's eye is taken off of the horizontal alignment bubble of the level 36 to determine whether the level end 40 is aligned with the X-mark 32, the worker 24 may inadvertently allow either end of the level 36 to move up or down, thereby throwing the level 36 out of horizontal alignment. If this occurs, the worker 24 may believe that the end 40 is at the same vertical level as the transducer unit 10 when this is not true. The prior art method thus may result in inconsistent and inaccurate alignment of the transducer unit 10 with the patient's right atrium 18.

OBJECTS OF THE INVENTION

From the foregoing it should be apparent that a primary object of the present invention is to provide improved apparatus and methods for measuring CVP of a medical patient.

Another important, but more specific, object of the present invention is to provide methods and apparatus for measuring CVP that provide a favorable mix of the following factors:

a. accurately and consistently vertically aligning the pressure transducer unit with a desired point on the patient;

b. allowing the transducer unit to be quickly vertically aligned by one worker;

c. allowing one alignment apparatus to be used with a plurality of transducer units;

d. reducing the costs of manufacturing and servicing the alignment apparatus; and e. allowing existing pressure transducers and alignment devices to be used.

Additional objects and advantages of the present invention will become apparent from the following description and accompanying drawings.

SUMMARY OF THE INVENTION

There have been invented, and disclosed herein, a new and novel pressure measuring apparatus. More particularly, the present invention comprises: (a) means for measuring the pressure within the fluid containing means; (b) fluid containing means connected between the pressure measuring means and a place at which the pressure of the bodily fluids is to be measured; (c) means for generating a beam of light; (d) housing means adapted to contain the light generating means; (e) means for determining that the beam of light is horizontally aligned; (f) means for vertically aligning the beam of light with a given measuring point on the pressure measuring means; and (g) means for selectively locking the housing means to prevent movement thereof relative to the pressure measuring means when the beam of light is both horizontally aligned and vertically aligned with the given measuring point on the pressure measuring means. When the given point on the pressure measuring means is vertically aligned with a desired point corresponding to the place at which the pressure is to be measured, the light generating means causes light to reflect off of the patient at the desired point.

The apparatus of the present invention may further comprises: (a) means for mounting the pressure measuring means at a fixed vertical level; and (b) means for so attaching the housing means to the mounting means that the housing means may be moved to a position where the beam of light is both horizontally aligned and vertically aligned with the pressure measuring means. In this case, the locking means comprise a screw means extending through the housing means and operatively engaging the mounting means to prevent relative movement between the housing means and the mounting means. The attaching means may comprise: (a) a flanged projection formed on the housing means; and (b) a pair of flanged rails attached to the mounting means, where the flanged projection is slideably received between the flanged rails. The apparatus may further comprise a clip means that may be securely attached to the mounting means, where the attaching means attach the housing to the mounting means through the clip means. The above-described mounting means may comprise a vertically extending pole and a bracket means slideably attached to the pole, where the attaching means attaches the housing to the bracket means.

Preferably, in the above-described apparatus, the vertical aligning means comprises an indicating means formed on the housing means. In this case, the beam of light is vertically aligned with the given point on the pressure measuring means when the indicating means is vertically aligned with the given point on the pressure measuring means. The horizontal alignment means preferably comprises at least one leveling tube having a leveling axis that is substantially parallel to the beam of light, the leveling tube comprising a closed transparent envelope, which contains a liquid and a bubble of gas, and lines formed on the envelope, where the leveling axis is substantially horizontally aligned when the bubble of gas is located between the two lines.

The present invention may also be embodied in an apparatus for vertically aligning a given point on a transducer unit that generates a signal corresponding to a pressure of a patient's bodily fluid with a desired point corresponding to a place at which the pressure is to be measured, the apparatus comprising:(a) means for generating light; (b) housing means adapted to contain the light generating means; (c) first and second leveling tubes each having a leveling axis that is substantially parallel to a path of the light generated by the light generating means, each leveling tube comprising (i) a closed transparent envelope containing a liquid and a bubble of gas; and (ii) lines formed on the envelope, where the leveling axis is substantially horizontally aligned when the bubble of gas is located between the two lines; (d) indicating means formed on the housing means, where the light path is vertically aligned with the given point when the indicating means is vertically aligned with the given point; and (e) means for selectively locking the housing means to prevent movement thereof relative to the given point when the light path is both horizontally aligned and vertically aligned with the given point In this embodiment, the first leveling tube is so mounted on a first end of the housing that, when the light path extends in a first direction, the light path may be horizontally aligned by rotating the housing until the bubble of the first leveling tube is located between the two lines of the first leveling tube. Similarly, the second leveling tube is so mounted on a second end of the housing that, when the light path extends in a second direction, the light path may be horizontally aligned by rotating the housing until the bubble of the second leveling tube is located between the two lines of the second leveling tube. One of the transducer unit and the patient are vertically displaced relative to the other of the transducer unit and the patient until the light generating means causes light to reflect off of the desired point, indicating that the given point is vertically aligned with the desired point.

The present invention may also be embodied in a method of measuring a pressure of a bodily fluid of a patient, the method comprising the steps of: (a) providing means for generating light; (b) providing pressure measuring means for measuring the pressure of the bodily fluid, the pressure measuring means having a given point thereon that must be vertically aligned with a desired point corresponding to the place at which the pressure is to be measured; (c) horizontally aligning a path of the light generated by the light generating means; (d) vertically aligning the light path with the given point on the pressure measuring means; (e) preventing relative movement between the light generating means and the pressure measuring means when the light path is both horizontally aligned and vertically aligned with the given point on the pressure measuring means; and (f) adjusting the vertical level of one of the pressure measuring means and the patient until the light generating means causes light to reflect off of the patient at the desired point Because the pressure measuring means may be located on either side of the patient, this method preferably further comprising the steps of: (a) providing a housing adapted to contain the light generating means; (b) providing first and second alignment means for executing the step of horizontally aligning the beam of light, where the first alignment means is mounted on one end of the housing and the second alignment means is located on the other end of the housing; and (c) horizontally aligning the beam of light with the first alignment means when the pressure transducer is located on one side of the patient and horizontally aligning the beam of light with the second alignment means when the pressure transducer is located on the other side of the patient In all of the above-mentioned embodiments, the light generating means is preferably a laser.

DETAILED DESCRIPTION OF THE PREFERRED EMBODIMENT

The present method of and apparatus for measuring central venous pressure will now be generally described with reference to FIGS. 2-8. In the following discussion, the terms "upper", "lower", and "vertical" refer to the directions to the top and bottom, respectively, of FIGS. 2 and 4, while the terms "front" and "back" refer to the directions to the lower left and upper right, respectively, in those figures. The terms "left", "right", "horizontal", and "sideways" refer the corresponding directions from the perspective shown in FIG. 2.

Figure 2:
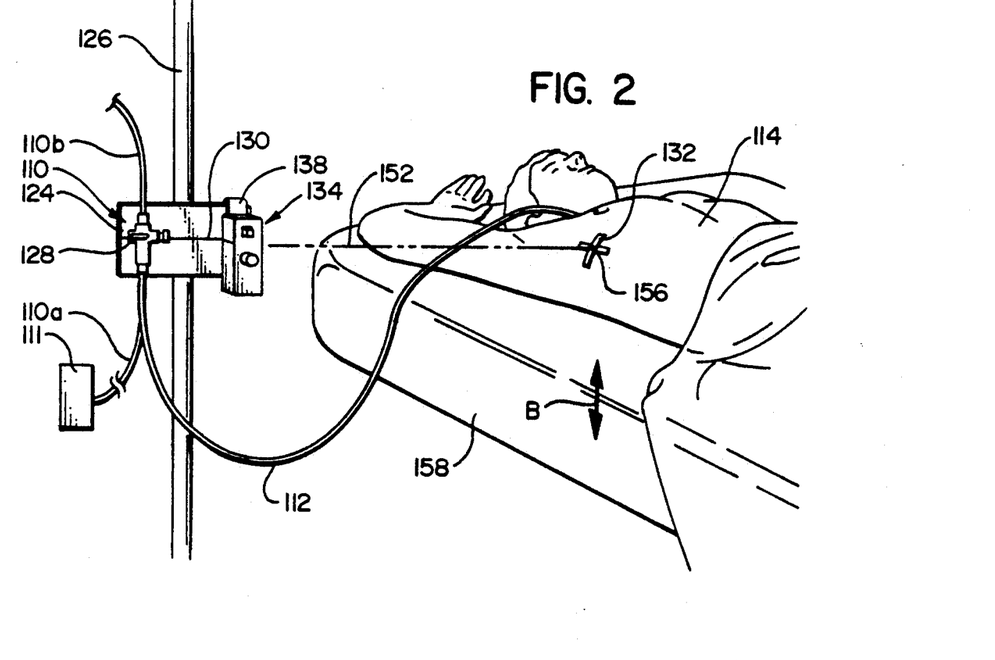
FIG. 2 is a perspective, environmental view depicting the method of the present invention for measuring a patient's central venous pressure.

In FIG. 2, the pressure monitoring device is a transducer unit indicated at reference character 110. The transducer 110 may be, for example, a transducer model number TXX-R Pressure Transducer 3CC manufactured by Viggo Spectromed. This transducer may be purchased in the 60 inch transducer kit for pole mount applications, model number T4812AD-4 also manufactured by Viggo Spectromed.

A length of IV connecting tubing 112 extends from a patient 114 to the transducer unit 110. As depicted in FIG. 3, a catheter 116 has been inserted into the patient's subclavian vein and threaded through this vein into the right atrium 118 of the patient's heart 120. The catheter 116 is connected at 122 to the IV connecting tubing 112. The catheter 116 and IV tubing 112 are filled with fluid; thus, the pressure of blood in the right atrium 118 is transmitted to the fluid within the catheter 116 and tubing 112 where the pressure can easily be measured by the transducer 110.

Referring back to FIG. 2, the transducer unit 110 is attached to a mounting bracket 124 which is slideably and rotatably mounted on a vertically extending pole 126. The vertical level of a given measuring point 128 of the transducer unit 110 is indicated by a line 130 formed on the bracket 124. In the preferred embodiment, the measuring point 128 is at the balancing port of the transducer unit 110.

The transducer unit 110 further comprises a cable 110a through which electrical signals related to sensed pressure are transmitted to an analyzing device 111 that calculates and records CVP based on these electrical signals. The analyzing device 11 may be, for example, a CVP module model number M1006A manufactured by Hewlett Packard and designed to be plugged into Hewlett Packard's Component Monitoring System model number 56-M117A.

A second length of IV connecting tubing 110b extends from the top of the transducer unit 110 to container (not shown) containing an IV solution to be introduced into the patient 114. This allows fluid within the tubing 112 to be flushed and allows introduction of intravenous fluids and medications into the patient's bloodstream as necessary.

The vertical level of the right atrium 118 of the patient's heart 120 generally corresponds to the midaxillary line of the patient 114 and is marked by an X-mark 132 formed on the patient 114 approximately 5 cm below the patient's sternum While this X-mark may not be precisely aligned with the patient's right atrium in all cases, the X-mark is actually formed on the patient with indelible ink so that measurements may at least be consistent over time.

Figure 4:
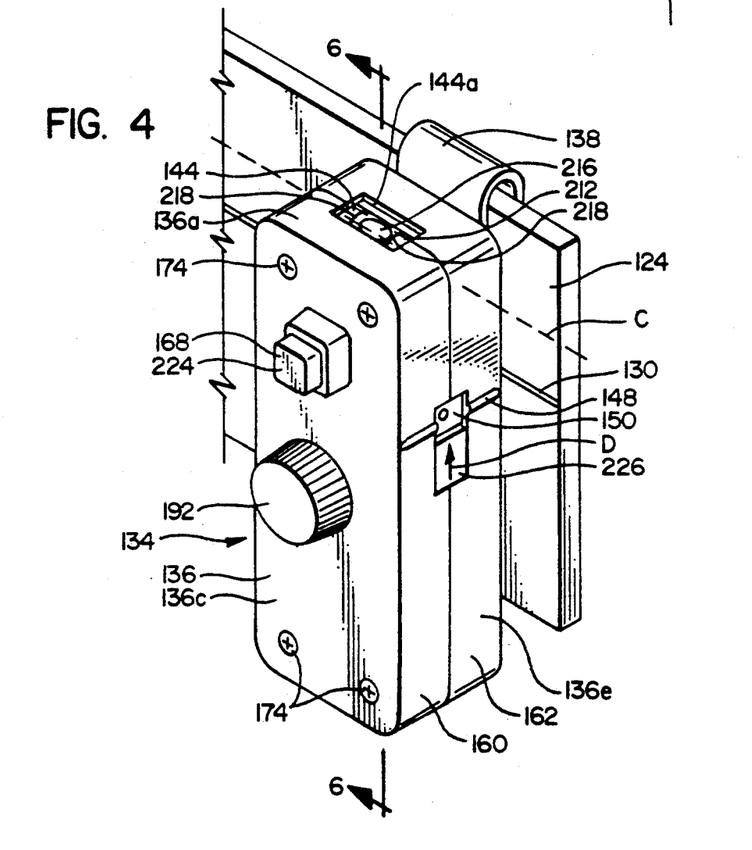
FIG. 4 is a perspective view of an alignment apparatus constructed in accordance with the present invention, the apparatus depicted as it would be oriented when placed to the left side of a patient.
Figure 8:
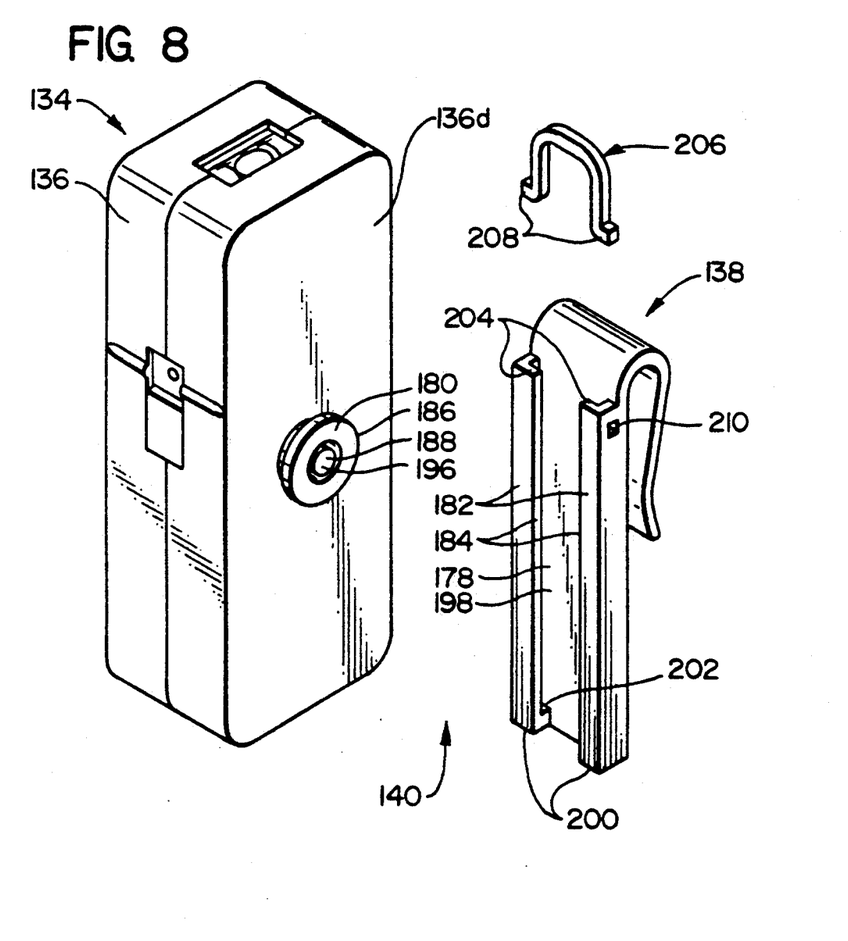
FIG. 8 is a perspective, view depicting the components of the attachment system of the alignment device of the present invention.

Indicated at 134 is an alignment device used by a health care worker (not shown) to vertically align the pressure transducer unit 110 with the X-mark 132. The alignment device 134 basically comprises: (a) a housing 136 (FIG. 4); (b) a clip 138 (FIGS. 4,6) for attaching the housing 136 to the transducer bracket 124; (c) an attachment system 140 (FIG. 8) for attaching the clip 138 to the housing 136; (d) a light source 142 (FIG. 6) mounted within the housing 136; (e) upper and lower leveling tubes 144 (FIGS. 4,6) and 146 (FIGS. 5,6) mounted to the upper wall 136a and lower wall 136b, respectively, of the housing 136; (f) an indicating mark 148 (FIGS. 4,5) for indicating an aperture 150 through which a beam of light, emanating from the light source 142, extends along a path 152 (FIG. 2); and (g) a locking system 154 (FIG. 6) for preventing or allowing relative movement between the housing 136 and the clip 138.

The pressure transducer 110, analyzing device 111, IV tubing 112, catheter 116, and alignment device 134 comprise the CVP pressure measuring apparatus of the present invention.

The above described pressure CVP pressure measuring apparatus is used to measure CVP in the following manner. Initially, transducer bracket 124 is mounted on the pole 126, and the transducer 110, which is attached to the analyzing device 111 through the cable 110a, is mounted on the transducer bracket 124. The IV tubing 112 is then connected between the transducer 110 and the catheter 116.

Next, the clip 138 is attached to the housing 136 by the attachment system 140. The housing 136 is then attached to the transducer bracket 124 by the clip 138. The locking system 154 is then loosened to allow relative movement between the housing 136 and the clip 138. The housing 136 is then moved so that: (a) the indicator mark 148 is vertically aligned with the line 130 on the transducer bracket 124 or directly with the measuring point 128 on the transducer unit 110; and (b) the leveling tubes 144 and 146 indicate that the housing upper and lower walls 136a and 136b are horizontally aligned.

Next, the light emanating from the light source 142 causes a point 156 of light to reflect off of the patient 114. The light source 142 is so mounted within the housing 136 that the housing upper and lower walls 136a and 136b are parallel to the light path 152. Accordingly, the light point 156 is at the same vertical level as the measuring point 128 and is used to vertically align the measuring point 128 with the center of the X-mark 132. Specifically, either the transducer bracket 124 or the bed 158 in which the patient 114 is lying may be so raised or lowered, as indicated by the arrow B, that the light point 156 coincides with the center of the X-mark 156.

The transducer 110 and analyzing device 111 may then be used to accurately and consistently measure and record the CVP of the patient 114.

Because the health care worker's hands are free once the alignment device 134 is attached to the transducer bracket 124 and adjusted as described above, a single health care worker can easily and quickly align the measuring point 128 with the X-mark 156.

Further, the light point 156 is continually shining on the patient 114 during the process of adjusting the height of the bed 158 or the bracket 124, unlike in the prior art where it was necessary for a single worker 34 to set the carpenter's level 136 down during the process of adjusting the height of the bed 158 or bracket 124. This significantly reduces the chances that the transducer measuring point 128 will be inaccurately aligned with the X-mark 132.

The clip 138, attachment system 140, and locking system 154 also allow the alignment device 134 of the present invention to be used on with a plurality of pressure transducers 110. These features thus allow a hospital facility to purchase a small number of these devices 134 for use in aligning a large number of transducers 110.

Finally, the alignment device 134 of the present invention may be easily constructed from a small number of, for the most part, relatively inexpensive parts. The alignment device 134 may thus be relatively cheaply manufactured.

The operation and construction of the alignment device 134 of the present invention will now be more specifically described with reference to FIGS. 2-8.

The housing 136 of the alignment device 134 comprises a front portion 160 and a rear portion 162. These housing portions 160 and 162 may be easily and inexpensively manufactured by the injection molding process. Holes 164 and 166 (FIG. 6) are formed in the housing front portion 160 to allow an ON/OFF button switch 168 and a shaft 170 (FIG. 6) of the locking system 154 to extend through a front wall 162c of the housing 136. A hole 172 is also formed in the back wall 162d of the housing 136 through which the locking system shaft portion 170 extends. The two housing portions 160 and 162 are held together by screws 174.

Figures 5, 6, 7:
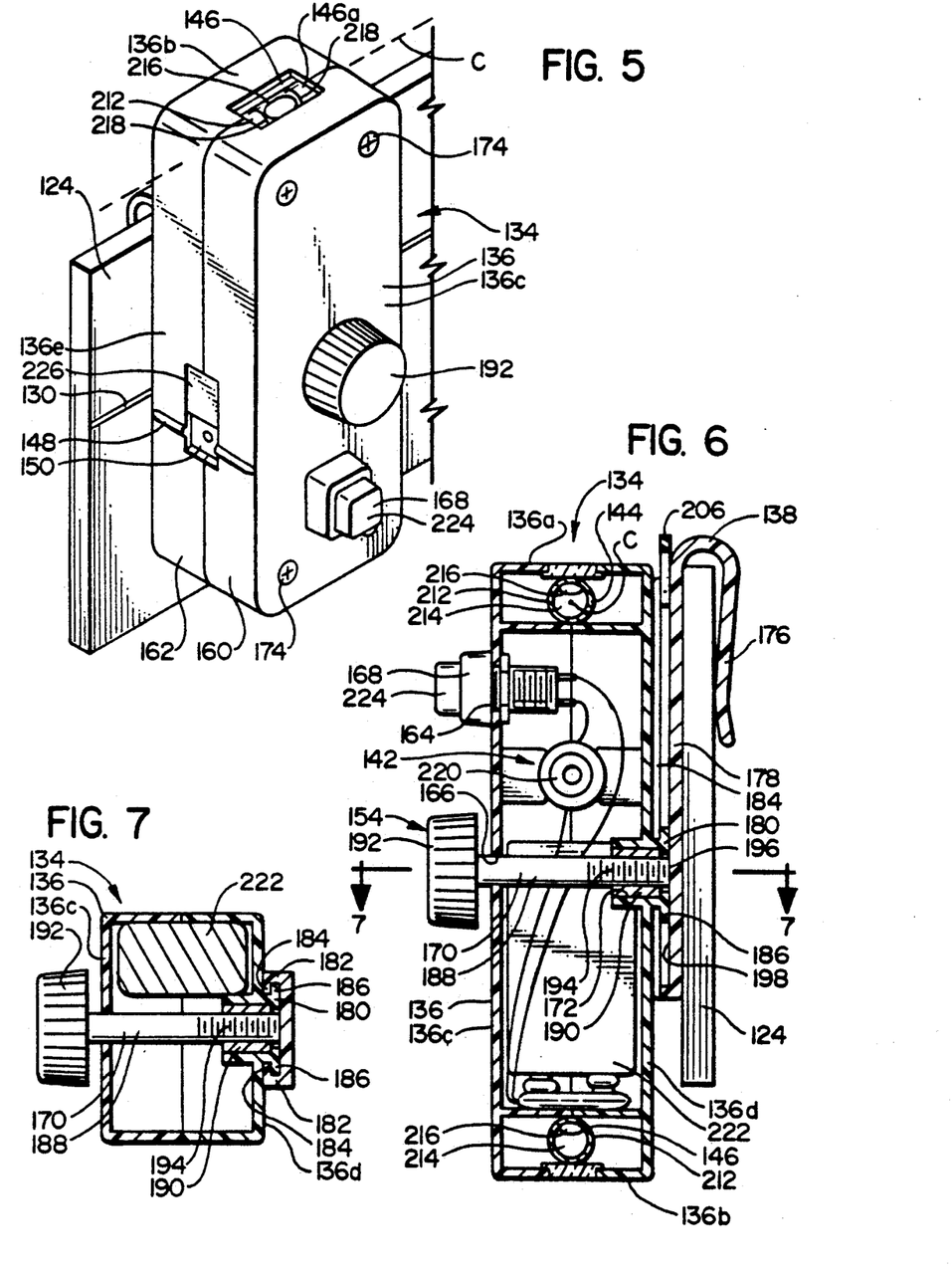
FIG. 5 is a perspective view of an apparatus constructed in accordance with the present invention, the apparatus depicted as it would be oriented when placed to the right side of a patient.
FIG. 6 is a side cut-away view of the alignment apparatus of present invention taken along lines 6 in FIG. 4.
FIG. 7 is a top cut-away view of the alignment apparatus of the present invention taken along lines 7 in FIG. 6.

The above-mentioned clip 138 is made of relatively rigid resilient material such as plastic. As is shown in FIG. 6, back portion 176 and front portion 178 of the clip 138 resiliently grip the transducer bracket 124 therebetween when the clip is used to attach the housing 136 to this bracket 124.

The attachment system 140 basically comprises a flanged projection 180 formed on a back wall 136d of the housing 136 and a pair of parallel rails 182 formed on the clip back portion 178. These rails 182 each have an inwardly directed flange portion 184. As is perhaps best shown in FIG. 7, the space between these flange portions 184 and the clip front portion 178 so receives the flange 186 of the flanged projection 180 so that the the housing 136 can not move frontward, backward, or sideways relative to the clip 138. However, if the locking system 154, which will be described in further detail below, is loosened, the attachment system 140 allows up and down movement of the housing 136 relative to the clip 138. In the preferred embodiment, the flange 186 of the flanged projection 180 has a circular periphery; this circular shape further allows the housing 136 to rotate about an axis extending through the flanged projection 180 relative to the clip 138 when the locking system 154 is loosened.

The locking system 154 basically comprises a locking screw 188 and a sleeve 190. The locking screw 188 comprises the above-mentioned shaft 170 and a knob 192 to facilitate rotation of the shaft 170. The sleeve 190 is cylindrical and is secured within the hole 172 in the housing back wall 136d. The inner surface of the sleeve 190 is threaded to receive a threaded portion 194 of the screw shaft 170. By turning the knob 192 to rotate the shaft 170 about its axis within the sleeve 190, the screw 188 is axially translated frontward or backward.

The locking system 154 is tightened and locked by so turning the screw 188 that this screw 188 is axially backwardly translated until a back end 196 (FIG. 8) thereof firmly contacts a front surface 198 of the clip front portion 178. When the screw back end 196 contacts this front surface 198, the housing 136, and the flanged projection 180 which is integrally formed therewith, are forced towards the front. As shown in FIG. 7, this frontward movement causes the flange 186 to butt up against the flanges 184 on the rails 182. The friction between the flange 186 and flanges 184 substantially prevents relative movement between the housing 136 and the clip 138.

On the other hand, the locking system 154 is loosened and unlocked by so turning the screw 188 that the screw 188 is axially frontwardly translated until the screw back end 196 does not contact the front surface 198 of the clip front portion 178. In this case, the flange 186 does not butt up against the flanges 184 on the rails 182, and the locking system 154 thus does not prevent relative movement between the housing 136 and the clip 138.

In the preferred embodiment, the attachment system rails 182 are closed at their bottom ends 200 by stopping surfaces 202 and open at their upper ends 204. These surfaces 202 at the rail bottom ends 200 contact the flange 186 on the flanged projection 180 to prevent this projection 180 from passing through the ends 200. Because the rail upper ends 204 are open, however, the flange projection may pass through these upper ends 204, allowing the housing 136 to be detached from the clip 138.

To close off these ends 204 and prevent the housing 136 from being removed from the clip 138, a stop member 206 may be provided. This stop member 206 is an integrally formed U-shaped resilient member with detents 208 formed at the open end of the U. These detents 208 may be moved towards each other so that they may be placed between the rails 182 and the flanges 184 thereof. The resiliency of the stop member 206 causes the detents 208 to move away from each other into holes 210 in the rails 182. When the detents 208 are engaged in the holes 210, the rail ends 204 are blocked to prevent the flanged member 180 from passing therethrough. It should be clear that the stop member 206 may be removed by pressing the detents 208 together so that they are retracted from the holes 210 and lifting the member 206 out from between the rails 182.

The above-mentioned leveling tubes 144 and 146 are essentially the same as the well-known leveling tubes employed by devices such as a carpenter's level These tubes 144 and 146 are located within the housing 136 at the upper and lower ends thereof. More particularly, these tubes 144 and 146 are mounted on the housing upper wall 136a and lower wall 136b, respectively, so that they are visible through holes 144a and 146a in these walls 136a and 136b. These holes 144a and 146a are formed along the parting line between the housing portions 160 and 162 to facilitate the manufacture of the housing 136.

As best shown in FIGS. 4-6, these leveling tubes 144 and 146 basically comprise a closed glass envelope 212 containing a fluid 214 and a bubble 216 of air or other gas. Two lines 218 are marked on the envelope 212. When a longitudinal axis C of these tubes 144 and 146 is horizontally aligned, the bubble 216 is between the lines 218. The axes C of the tubes 144 and 146 is shown horizontally aligned in FIGS. 4 and 5.

In the preferred embodiment, the tubes 144 and 146 are so mounted within the housing 136 that the axes C thereof are substantially parallel to the housing upper and lower walls 136a and 136b. Further, the above-mentioned light source 142 is mounted within the housing 136 such that the path 152 of the light emanating therefrom is also substantially parallel to the housing walls 136a and 136b. Accordingly, when the leveling tubes 144 and 146 indicate that the axes C thereof are substantially horizontally aligned, the light path 152 is also substantially horizontally aligned.

The light source 142 basically comprises a laser 220, the ON/OFF switch 168 briefly mentioned above, and an energy source 222. The laser 220 is preferably a diode type laser such as the laser models VLM2-5, VLM2-5C, or VLM2-5R, manufactured by Applied Laser Systems, which are currently available in the market. The battery 222 is a conventional 9 volt battery. The switch 168 is a conventional push-button, lighted switch that is so electrically connected between the energy source 222 and the laser 220 that successively pressing a button portion 224 of the switch 168 alternately prevents and allows current-flow through the laser 220. When current flows through the laser 220, a lamp within the button portion 224 glows to indicate that the laser 220 is operating.

The above-mentioned indicator mark 148 is a narrow ridge formed on the right side 136e of the housing 136. This mark 148 extends on either side of the aperture 150 to indicate where the light path 152 passes through the aperture 150. The light path 152 is vertically aligned with the given point 128 on the transducer unit 110 when this mark 148 is even with the line 130 on the transducer bracket 124.

The above-mentioned orifice 150 for allowing the light path 152 to pass out of the housing 136 is formed along the parting line of the housing portions 160 and 162 to facilitate the molding of these portions 160 and 162. The alignment device 134 also comprises a door 226 that may be moved in the direction of the arrow D in FIG. 4 to cover this orifice 150.

The method of using the above-described CVP pressure measuring device will now be described in further detail. This method will first be described with reference to FIGS. 2 and 4, in which the vertical pole 126 is located to the left of patient's bed 158.

Initially, the housing 136 is attached to the clip 138 by inserting the flanged projection 180 into the open rail upper ends 204. The stop member 206 is then placed between the rails 182 so that the detents 208 thereof engage the holes 210 in the rails 182. The attachment system 140 thus attaches the housing 136 to the clip 138.

The clip 138 is then so placed onto the transducer bracket 124 that the bracket 124 is securely gripped between the clip back and front portions 176 and 178.

The locking system 154 is then loosened by turning the knob 192 so that the end 196 of the screw 188 does not contact the front surface 198 of the clip front portion 178. The attachment system 140 and locking system 154 thus allow the housing 136 to moved up or down as necessary to align the indicating mark 148 with the line 130 on the bracket 124. The housing 136 may also be rotated as necessary to ensure that the bubble 216 of the upper leveling tube 144 is between the lines 218 on this tube 144. When the indicating mark 148 is aligned with the line 130 and the bubble 216 is between the lines 218, the knob is turned in the other direction until the screw end 196 abuts the clip front portion front surface 198, thus locking the alignment device 134 relative to the transducer unit 110.

The door 226 is then moved into its open position where it does not cover the orifice 150. The button 224 is then pressed to energize the laser 220. The path 152, which is horizontally aligned, of the light emanating from the laser 220 extends through the orifice 150. The light spot 156 reflects off of a surface such as the patient 114, the bed 158, or a wall on the opposite side of the patient from the alignment device 134, thereby indicating whether the patient 114 needs to be raised or lowered relative to transducer unit 110 to align the measuring point 128 on the transducer unit 110 with the X-mark 132 formed on the patient 114. Either the patient 114 may be moved up or down by raising and lowering the bed 158 or the transducer unit 110 may be moved up or down by raising or lowering transducer bracket 124 on the pole 126. It may also be necessary to rotate the bracket 124 around the pole 126 so that the light beam 152 and the X-mark 132 are in the same vertical plane.

In any event, when the light point 156 reflects off of the patient 114 at the center of the X-mark 132, the transducer measuring point 128 is vertically aligned with the X-mark 156. At this point, the leveling tube 144 and indicating mark 148 may be checked to verify that the light beam 152 is both horizontally aligned and vertically aligned with the transducer measuring point 128.

The analyzing device 111 may then be used to analyzes the signals generated by the transducer 110 to determine the CVP of the patient 114.

The method of and apparatus for measuring CVP is essentially the same in the situation where the pole 126 and bracket 124 are located on the right side of the patient's bed 158. The primary difference is that the alignment device 134 is so rotated relative to the transducer bracket 124 that, as shown in FIG. 5, the light beam 152 propagates in the opposite direction. This may be accomplished simply by loosening the locking system 154 and rotating the housing 180° relative to the bracket 124. In this situation, the light beam 152 is horizontally aligned by aligning the bubble 216 of the bottom leveling tube 146 with the lines 218 thereof because the tube 146 will be facing upwardly.

From the foregoing, it should be clear that the present invention may be embodied in forms other than those disclosed above without departing from the spirit or essential characteristics of the present invention.

For example, in the preferred embodiment, the rails 182 of the attachment system 140 are integrally formed on the clip 138, which is in turn attached to the transducer bracket 124. Alternatively, these rails 182 may be mounted directly on the bracket 124. In this case, the rails 182 may be formed with the stopping surfaces 202 so located that the indicating mark 148 is aligned with the line 130 when the flanged projection 180 comes into contact with these surfaces 202.

Further, while the light source 142 comprises a laser 220 that generates coherent electromagnetic radiation, a non-coherent light source may be used with appropriate lenses for focusing the light beam thereof to produce a light spot of sufficiently small size for the purposes of the present invention.

In another form, the flanged projection 180 may have a rectangular perimeter configuration. This configuration would allow the housing 136 to be rotated relative to the clip 138 only through a small angle; however, this small angle would in most cases be sufficient to horizontally align the light beam 152. This configuration would provide greater surface contact between the flange 186 on the flanged projection 180 and the flanges 184 on the rails 182, resulting in greater strength against possible over tightening of the locking system screw 188.

Further, in an alternative embodiment, the alignment device 134 may include means for adjusting the angle between the light beam 152 and the axes C of the leveling tubes 144 and 146. These means would allow the device 134 to be calibrated.

The preferred embodiment also includes a simple electrical circuit comprising only the laser 220, the switch 168, and the power source 222. Optionally, a timing circuit may be provided for shutting off current to the laser 220 after a predetermined length of time or a power level indicating circuit may be provided for indicating when the power source 222 is becoming depleted.

The above-described embodiment is therefore to be considered in all respects illustrative and not restrictive, the scope of the invention being indicated by the appended claims rather than the foregoing description. All changes that come within the meaning and scope of the claims are intended to be embraced therein.

I claim:

1. An apparatus for vertically aligning a given point on a transducer unit that generates a signal corresponding to a pressure of a patient's bodily fluid with a desired point corresponding to a place at which the pressure is to be measured, the apparatus comprising;
   a. means for generating light;
   b. housing means adapted to contain the light generating means;
   c. first and second leveling tubes each having a leveling axis that is substantially parallel to a path of the light generated by the light generating means, each leveling tube comprising
      i. a closed transparent envelope containing a liquid and a bubble of gas; and
      ii. lines formed on the envelope, where the leveling axis is substantially horizontal when the bubble of gas is located between the two lines;
   d. an indicating mark formed on the housing means, where the light path is vertically aligned with the given point when the indicating mark is vertically aligned with the given point; and
   e. means for selectively locking the housing means to prevent movement thereof relative to the given point when the light path is both horizontally and vertically aligned with the given point; wherein
   the first leveling tube is so mounted on a first end of the housing that, when the light path extends in a first direction, the light path may be rendered horizontal by rotating the housing until the bubble of the first leveling tube is located between the two lines of the first leveling tube;
   the second leveling tube is so mounted on a second end of the housing that, when the light path extends in a second direction, the light path may be rendered horizontal by rotating the housing until the bubble of the second leveling tube is located between the two lines of the second leveling tube; and
   one of the given point and the desired point are vertically displaced relative to the other of the given point and the desired point until the light generating means causes light to reflect off of the desired point, indicating that the given point is vertically aligned with the desired point.

2. The apparatus as recited in claim 1, further comprising:
   a. means for mounting the given point at a fixed vertical level;
   b. means for so attaching the housing means to the mounting means that the housing means may be moved to a position where the light path is both horizontal and vertically aligned with the given point.

3. The apparatus as recited in claim 2, further comprising a clip that may be securely attached to the mounting means, where the attaching means attach the housing means to the mounting means through the clip.

4. The apparatus as recited in claim 3, in which the attaching means comprises;
   a. a flanged projection formed on one of the housing means and the clip; and
   b. a pair of flanged rails integrally formed on the other of the housing means and the clip, where the flanged projection is slideably received between the flanged rails.

5. The apparatus as recited in claim 4, in which the locking means comprise a threaded member extending through the housing means and operatively engaging the clip to prevent relative movement between the housing means and the clip.

6. The apparatus as recited in claim 5, in which the mounting means comprises a vertically extending pole and a transducer bracket slideably attached to the pole, where the attaching means attaches the housing means to the transducer bracket.

7. The apparatus as recited in claim 1, in which the light generating means is a laser.

8. A method of measuring a pressure of a bodily fluid of a patient, the method comprising the steps of:
   a. providing means for generating light;
   b. providing pressure measuring means for measuring the pressure of the bodily fluid, the pressure measuring means having a given point thereon that must be vertically aligned with a desired point corresponding to the place at which the pressure is to be measured;
   c. providing a housing adapted to contain the light generating means;
   d. providing first and second alignment means for rendering the beam of light horizontal, where the first alignment means is mounted on one end of the housing and the second alignment means is located on the other end of the housing; and
   e. rendering the beam of light horizontal using the first alignment means when the housing is located on a first side of the patient and using the second alignment means when the housing is located on a second side of the patient;
   f. vertically aligning the light path with the given point on the pressure measuring means;
   g. preventing relative movement between the light generating means and the pressure measuring means when the light path is both horizontally and vertically aligned with the given point on the pressure measuring means; and
   h. adjusting the vertical level of one of the pressure measuring means and the patient until the light generating means causes light to reflect off of the patient at the desired point.

9. An apparatus for measuring the pressure of bodily fluids in a medical patient, the apparatus comprising:
   a. fluid containing means for allowing fluid to flow from a place at which the pressure of the bodily fluids is to be measured to a measuring point;
   b. means for measuring the pressure within the fluid containing means at the measuring point;
   c. means for generating a beam of light;
   d. housing means for containing the light beam generating means;
   e. means for determining that the beam of light is substantially horizontal;
   f. a transducer bracket on which the pressure measuring means is mounted;
   g. an intermediate member;
   h. means for securely attaching the intermediate member to the transducer bracket;
   i. mounting means for mounting the housing means to the intermediate member comprising locking means operable between a first position in which the housing means may be moved relative to the intermediate member so that the beam of light is substantially horizontal and substantially vertically aligned with the measuring point and a second position in which the locking means operatively engages the intermediate member to prevent relative movement between the housing means and the intermediate member when the beam of light is substantially horizontal and substantially vertically aligned with the measuring point;
   j. means for allowing at least one of the patient and the transducer bracket to be vertically displaced until the light generating means causes light to reflect off of the patient at a desired point on the patient corresponding to the place at which pressure is to be monitored.

10. The apparatus as recited in claim 9, in which the locking means comprises a threaded member extending through the housing means and rotatable to engage the intermediate member when the locking means is in the second position.

11. The apparatus as recited in claim 9, in which the vertical aligning means comprises an indicating mark formed on the housing means, where the beam of light is vertically aligned with the given point on the pressure measuring means when the indicating mark is vertically aligned with the given point on the pressure measuring means.

12. The apparatus as recited in claim 9, in which the means for determining that the beam of light is substantially horizontal comprises at least one leveling tube having a leveling axis that is substantially parallel to the beam of light, the leveling tube comprising a closed transparent envelope, which contains a liquid and a bubble of gas, and lines formed on the envelope, where the leveling axis is substantially horizontal when the bubble of gas is located between the two lines.

13. The apparatus as recited in claim 9, in which the mounting means further comprises:
   a. a flanged member extending from one of the housing means and the intermediate member; and
   b. a pair of flanged rails formed on the other of the housing means and intermediate member, where a groove is formed between the flanged rails and the flanged member is slideably received in the groove in a manner that allows rotation of the housing means about an axis and vertical displacement of the housing along the length of the groove.

14. The apparatus as recited in claim 9, in which the means for securely attaching the intermediate member to the transducer bracket comprises clip means formed on one of the transducer bracket and the intermediate member for clipping the one end of the transducer bracket and the intermediate member to the other of the transducer bracket and the intermediate member.

15. The apparatus as recited in claim 9, in which the light generating means is a laser.

16. An apparatus for measuring the pressure of bodily fluids in a medical patient, the apparatus comprising:
   a. fluid containing means for allowing fluid to flow from a place at which the pressure of the bodily fluids is to be measured to a measuring point;
   b. means for measuring the pressure within the fluid containing means at the measuring point;
   c. means for generating a beam of light;
   d. housing means for containing the light beam generating means, the housing means being generally rectangular and having first and second end surfaces;
   e. first and second leveling means for determining that the beam of light is substantially horizontal, the first and second leveling means being mounted in the housing so that they are visible through the first and second end surfaces, respectively, and having first and second leveling axes that are substantially parallel to each other and to the beam of light;
   f. a transducer bracket on which the pressure measuring means is mounted;
   g. an intermediate member;
   h. means for securely attaching the intermediate member to the transducer bracket;
   i. mounting means for mounting the housing means onto the intermediate member comprising locking means operable between a first position in which the housing means may be moved relative to the intermediate member so that the beam of light is substantially horizontal and substantially vertically aligned with the measuring point and a second position in which the locking means operatively engages the intermediate member to prevent relative movement between the housing means and the intermediate member when the beam of light is substantially horizontal and substantially vertically aligned with the measuring point;
   j. means for allowing at least one of the patient and the transducer bracket to be vertically displaced until the light generating means causes light to reflect off of the patient at a desired point on the patient corresponding to the place at which pressure is to be monitored.

17. The apparatus as recited in claim 16, in which the locking means comprises a threaded member extending through the housing means and rotatable to engage the intermediate member when the locking means is in the second position.

18. The apparatus as recited in claim 16, in which the first and second means for determining that the beam of light is substantially horizontal each comprises a leveling tube, the leveling tube comprising a closed transparent envelope, which contains a liquid and a bubble of gas, and lines formed on the envelope, where the leveling axes are substantially horizontal when the bubble of gas is located between the two lines.

19. The apparatus as recited in claim 16, in which the mounting means further comprises:
  a. a flanged member extending from on one of the housing means and the intermediate member; and
  b. a pair of flanged rails formed on the other of the housing means and intermediate member, where a groove is formed between the flanged rails and the flanged member is slideably received in the groove in a manner that allows rotation of the housing means about an axis and vertical displacement of the housing along the length of the groove.

20. The apparatus as recited in claim 16, in which the means for securely attaching the intermediate member to the transducer bracket comprises clip means formed on one of the transducer bracket and the intermediate member for clipping the one of the transducer bracket and the intermediate member to the other of the transducer bracket and the intermediate member.

* * * * *